United States Patent [19]

Taguchi

[11] Patent Number: 4,615,333
[45] Date of Patent: Oct. 7, 1986

[54] RIGID ENDOSCOPE OF OBLIQUE WINDOW TYPE

[75] Inventor: Akihiro Taguchi, Hachioji, Japan

[73] Assignee: Olympus Optical Co., Ltd., Tokyo, Japan

[21] Appl. No.: 696,293

[22] Filed: Jan. 30, 1985

[30] Foreign Application Priority Data

Feb. 3, 1984 [JP] Japan ............................ 59-13649[U]

[51] Int. Cl.⁴ .............................................. A61B 1/06
[52] U.S. Cl. ................................................... 128/6
[58] Field of Search ................................. 128/5, 6, 7, 4

[56] References Cited

U.S. PATENT DOCUMENTS

| | | | |
|---|---|---|---|
| 3,278,738 | 10/1966 | Clark | 240/2 |
| 3,592,199 | 7/1971 | Ostensen | 128/6 |
| 4,361,139 | 11/1982 | Takagi | 128/6 |

FOREIGN PATENT DOCUMENTS 58-190913 11/1983 Japan .

*Primary Examiner*—William H. Grieb
*Attorney, Agent, or Firm*—Armstrong, Nikaido, Marmelstein & Kubovcik

[57] ABSTRACT

A lens tube capable to view obliquely forwards through an observation optical system having the oblique tip face inclined from a plane perpendicular to the longitudinal axis of tubular sheath tube comprising the outer periphery of probe of endoscope is arranged eccentrically from the central axis of the sheath tube and an illuminating optical system is arranged in the residual space between the lens tube and the sheath tube for transmitting the illuminating light and the outlet tip is formed into an oblique face inclined adversely to the inclination of oblique tip face of the lens tube, thereby issuing the illuminating light to the viewing direction of rigid endoscope of oblique window type.

5 Claims, 6 Drawing Figures

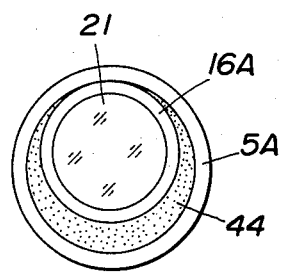
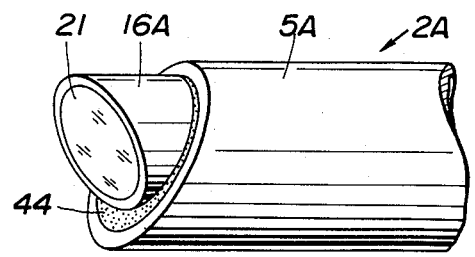
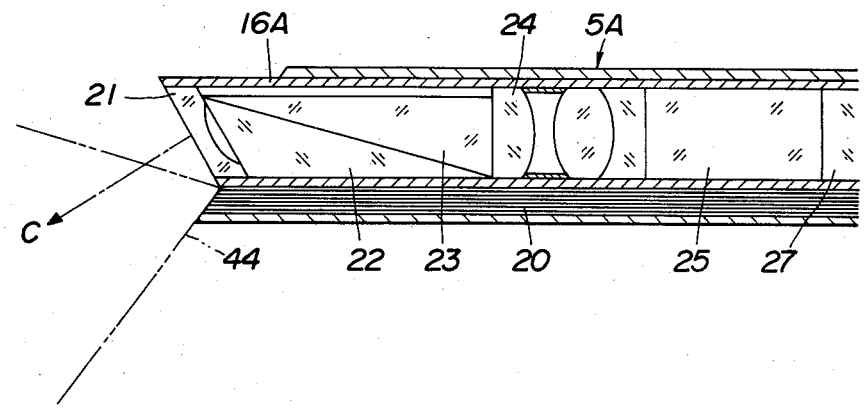
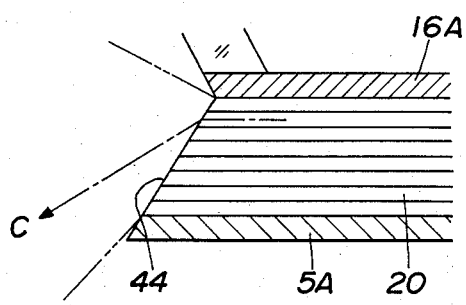
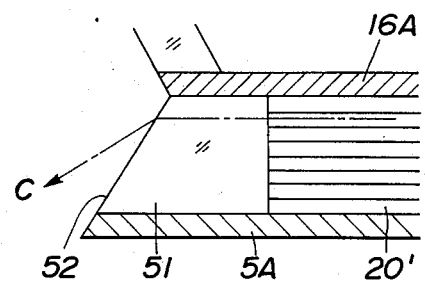

RIGID ENDOSCOPE OF OBLIQUE WINDOW TYPE

BACKGROUND OF THE INVENTION

The present invention relates to a rigid endoscope of oblique window type having improved distribution characteristics of illuminating light.

There have been employed endoscopes for the observation and diagnosis of an object such as organ or the like in a body cavity by inserting the elongated probe into the body cavity or the like for focusing the object by means of objective optical system formed at the tip of the probe.

Such endoscopes include flexible endoscope wherein the probe is flexible and adapted to observe the object in the body cavity through the oral cavity or the like and nonlinear passage and rigid endoscope wherein the probe is rigid and inserted substantially linearly.

Although such a rigid endoscope cannot be inserted easily through a flexible passage, it has an advantage that it provides more distinct image by employing image transferring means such as relay lens system or the like over those obtained by employing a flexible image guide fibre bundle. Because of the rigid structure, it is incompatible with the body cavity to limit the observable field so that the endoscope having visual direction such as straight window type or oblique window type should be chosen depending on the object to be observed.

As seen from a conventional embodiment as shown in Published Japanese Patent Application No. 190913/1983, an endoscope of oblique window type realizes desired light distribution characteristics so as to enable illumination over any desired range of view by bending the tip of the light guide inserted through the inserting probe, by means of a leading tip member, or the like, for transmitting and radiating the illuminating light or bending the tip of the pipe inserting light guide, or the like, therethrough and radiating the light through the output window of the light guide inserted through said bend portion, thereby illuminating the portion observable by the objective optical system in the oblique direction.

However, in such means, the outer diameter of the probe is relatively large and the tip member requires a space for receiving or attaching the tip member and has a large diameter. When the illuminating light is radiated to the desired direction by bending the tip member without damaging it, the means function efficiently. However, when a rigid endoscope having a fine diameter probe is employed, there is provided no space for attaching the tip member as set forth above or no sufficient bend when the tip member is inserted through a bended pipe. Thus, light distribution characteristics to the desired direction is not provided.

As prior art for radiating the illuminating light by deflecting to a desired direction, there has been known light deflecting means as shown in U.S. Pat. No. 3,278,738. According to this patent, the means are provided with a fibre bundle comprising an illuminating optical system around the objective optical system of microscope. The tip of the bundle is tilted to the outer periphery side with respect to the radial direction, thereby deflectioning the illuminating light guided through the fibre bundle so as to concentrate the light to the object to be observed through the inclined window at the tip of bundle. This increases the intensity of illumination to the object to be observed for observing the object directly and effectively through the objective lens arranged at the tip of the objective optical system.

However, when light deflection means are applied to an endoscope of oblique window type, the objective lens should be arranged at the tip of the objective optical system so as to be tilted at a predetermined angle with respect to the central axis of said objective optical system, and with respect to the visual range to radiate the illuminating light to the visual direction. Hence, when such a structure is applied to an endoscope of oblique window type, it is impossible to radiate the illuminating light to the direction of object with the required intensity.

BRIEF SUMMARY OF THE INVENTION

It is a principal object of the present invention to provide rigid endoscope of oblique window type wherein the illuminating light can be issued effectively to the desired tilting direction even when the probe of the endoscope has a small diameter.

It is another object of the present invention to provide a rigid endoscope of oblique window type wherein the illuminating light to the visual range is provided through a simple structure incorporating a lens tube for receiving the objective optical system of an endoscope of oblique window type.

It is a further object of the present invention to provide a rigid endoscope of oblique window type which can illuminate the oblique range with low costs.

In short, the present invention provides a rigid endoscope of oblique window type structured so that the end surface of transparent member arranged at the outlet end of the light guide or at a leading zone from the outlet end is formed obliquely within the inside of an obliquely defined tip of a lens pipe incorporating the objective optical system in confronted relation to the obliquely defined tip, thereby enabling illuminating in the oblique direction over the observable range of image focussed by the objective optical system.

The following description will elucidate further characteristics and advantages achieved by the present invention.

BRIEF DESCRIPTION OF THE DRAWINGS

FIG. 1 to FIG. 5 illustrate a first embodiment of the present invention, wherein FIG. 1 is a longitudinally sectional view of rigid endoscope of oblique window type according to said first embodiment, FIG. 2 is a front view showing the tip of probe, FIG. 3 is a perspective view of the tip of probe, FIG. 4 is an enlarged longitudinally sectional view of the tip of probe shown in FIG. 1, FIG. 5 is a further enlarged longitudinally sectional view of periphery of tip of probe shown in FIG. 4, and FIG. 6 is a longitudinally sectional view of periphery of tip of light guide according to a second embodiment.

DETAILED DESCRIPTION

Figure 1:
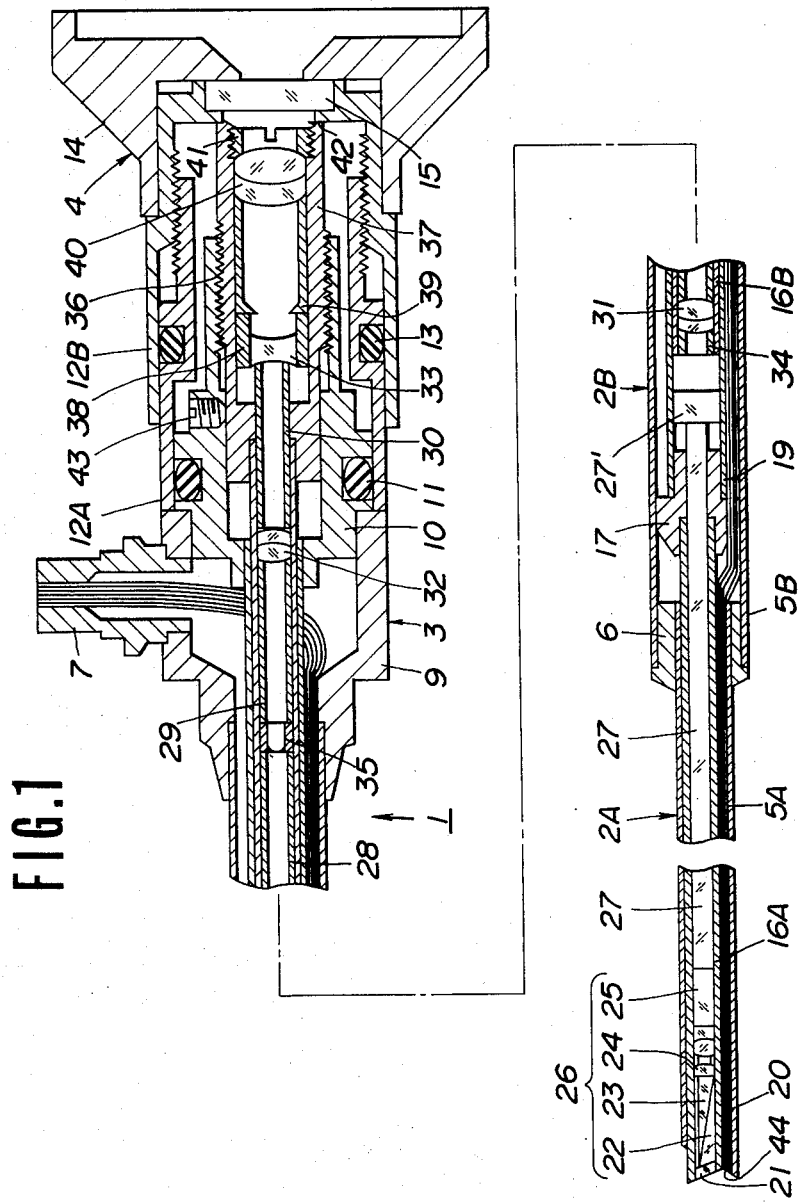

As shown by FIG. 1, the rigid endoscope of oblique window type 1 according to the first embodiment comprises a first elongated probe 2A capable to be inserted through a body cavity, a second probe 2B having a larger diameter than that of said probe 2A, a manipulating knob 3 connected to the trailing end of said probe 2A and having a larger diameter than that of said probe 2A, and an eyepiece 4 attached to the trailing end of said manipulating knob 3.

The first probe 2A is coated with sheath pipe 5A which is rigid and has a small diameter. The trailing end of sheat pipe 5A is connected through flange 6 with a second sheath pipe 5B having a larger diameter than that of said sheath pipe 5A and the trailing end of sheath pipe 5B is secured to the inner periphery of leading open end of said manipulating knob 3 provided with mouthpiece 7 for light guide connected with light guide cable (not shown) by soldering or the like.

The trailing end of main body 9 comprising said manipulating knob 3 is connected to connector member 10 with an adhesive or by soldering, the outer periphery of leading end of the connector member 10 being fitted through the inner periphery of the trailing end of body 9. The outer periphery of connector member 10 is grooved for receiving a water-tight O-ring 11 and the outer periphery provided with the peripheral recess is covered with a first eyepiece cover 12A so as to fit the inner periphery of the leading end of cover 12.

The first eyepiece cover 12A is formed generally into a cylinder at the centre portion and the outer periphery of said cylinder is grooved into a pheripheral recess to receive a water-tight O-ring 13. The outer periphery of trailing end of the cover 12A is provided with male thread and a second eyepiece cover 12B is attached so that the inner periphery of second eyepiece cover is fitted through the outer grooved periphery of first eyepiece cover 12A and the female thread provided on the inner periphery of cover 12B is engaged with the male thread provided on the outer periphery of cover 12A. The outer periphery of trailing end of the second eyepiece cover 12B is secured to eyepiece 14 diverged to the trailing end by fitting adhesively the eyepiece through the outer periphery of trailing end of cover 12B. The inner periphery of the trailing end of second eyepiece cover 12B is attached with cover glass 15.

Within the sheath tube 5A comprising the probe 2A to be inserted actually into the body cavity, there is provided eccentrically a first lens tube 16, for example, an optical system receiver tube in contact with the upper inner periphery of said sheath tube 5A. The outer periphery of trailing end of lens tube 16A is fitted through a connector member 17 fitted through second sheath tube 5B. The trailing end of connector member 17 is fitted fixedly through inner tube 19 having a larger diameter than that of first lens tube 16A, through which a second lens tube 16B is inserted so as to be fitted through inner tube 19. The trailing end of inner tube 19 is fitted fixedly through the inner periphery of leading end of connector member 10 within manipulating knob 3 with an adhesive or by soldering or the like.

Through the space defined between first sheath tube 5A and first lens tube 16A and having a crescent cross-section as shown in FIG. 2, there is inserted light guide 20 comprising fine fibre bundle (i.e. optical fibre bundle) as transmitting means of illuminating light. The light guide 20 is inserted through second sheath tube 5B, bended outwards within main body 9 of manipulating knob and the trailing end thereof is fixed by light guide mouthpiece 7.

As shown by the enlarged views of FIGS. 3 and 4, the leading tip of lens tube 16A inserted through first sheath tube 5A is cut obliquely with respect to the axial direction of probe 2A and sealed by concave lens 21. Namely, the tip window and concave lens 21 of lens tube 16A define a portion inclined inwards from the inner periphery X of sheath tube 16A relative to the axis Y of such sheath tube 5A. As shown FIG. 4, Prisms 22, 23, convex lens 24, rod lens 25, etc. are arranged at the rear side of said concave lens 21 to form objective lens system 26 having viewing direction C which is perpendicular to the end surface of concave lens 21 and directed to obliquely downwards. In contact with said rod lens 25, there is inserted relay lens of refractive index ingredient type 27 through lens tube 16A so as to transmit the image focussed by said objective lens system at the backward position of first probe 2A. In place of the above-mentioned relay lens of refractive index ingredient type 27, the construction using fibre bundles can be available.

At the trailing end of said relay lens of refractive index ingredient type 27 and at the vicinity of leading end of said inner tube 19, there is secured firmly a thick cover glass 27' having a larger diameter than that of relay lens of refractive index ingredient type 27 and fitted through the inner periphery of inner tube 19 so that the central axis thereof is registered with the optical axis of said relay lens of refractive index ingredient type 27. The image transmitted by said relay lens of refractive index ingredient type 27 is transmitted through relay lens system comprising, for example, doublet lens 31, 32 maintained in positions by means of spacer rings 28, 29, 30, etc. in said second lens tube 16B having a larger diameter than that of first lens tube 16A so as to be focussed through field lens 33 at the front of iris 39 for throttling the view at the back of said field lens 33.

Lens 31 arranged at the leading end side of second lens tube 16B is secured fixedly by lens cover fixture 34 by pressure fitting or threading and an iris for throttling the light intensity 35 is provided between lens 31 and 32.

Second lens tube 16B can be inserted through said inner tube 19 and incorporated therein the relay lens system and the trailing end of said second lens tube 16B has an outer diameter fittable through the inner diameter of connector member 10 and it is fitted firmly through the inner periphery of leading end of eyepiece frame 37 provided with male thread 36 to be threaded through the female thread provided around the inner periphery of trailing end of said connector member 10.

Within said eyepiece lens frame 37, there are arranged field lens 33 through lens frame 38, iris 39 for throttling the view at the back of said field lens 33 and eyepiece lens 40 at the back of said iris 39, the eyepiece lens 40 being secured firmly by means of annular cover nut 41 so as to press the eyepiece lens formward. The distance of eyepiece lens 40 arranged within said eyepiece lens frame 37 from the front of iris 39 is set optionally.

In addition, field lens 33 is set so that when the image is observed in a manner that the eye is substantially contacted with eyepiece frame 14 under the condition that the leading end of end piece 42 having a radial protrusion engaged with the trailing end of second eyepiece cover 12B is abutted with the trailing end of eyepiece lens frame 37, the position is the best observable eyepoint without pressing the eye strongly against the eyepiece frame 14 for bring the eye excessively closely or without aparting the eye excessively from the frame.

In addition, the relay lens system within second lens tube 16B and the trailing end being secured firmly with said eyepiece lens frame 37 employs lens 31, 32 having larger and easy workable diameters than that of first lens tube 16A and spacer rings 28, 29, 30 having predetermined lengths so as to transmit the image through field lens 33 to at front of iris 39 for throttling the view range.

Second lens tube 16B inserted through said relay lens system and eyepiece lens frame 37 incorporated with the eyepiece lens system can be displaceable longitudinally by changing the length of threaded portion with respect to connector member 10 secured fixedly the inner tube 19. Accordingly, even when the relay lens system incorporating relay lens of refractive index ingredient type 27 inserted through first lens tube 16A is fluctuated in its length or in the image-transmitting position due to the dimensional fluctuation of such optical members, the inserted length of second lens tube can be adjusted by rotating second lens tube 16B inserted through inner tube 19 and the trailing end thereof being fixed to connector member to be displaced together with the eyepiece lens system and the second lens tube is fixed to the eyepiece lens frame 37 by means of set screw 43 threaded through the threaded hole bored into connector member 10. As shown by the enlarged views of FIGS. 4 or 5, the end window 44 for radiating the illuminating light from the tip of light guide 20 inserted through said probes 2A, 2B is cut, for example, obliquely together with sheath tube 5A so that the fibres are protruded to the viewing direction C, namely downwards in the figures at the end window. In other words, the illuminating light transmitted through the centres of fibres is refracted to the viewing direction C as shown in FIG. 5 by cutting the outlet end of illuminating light to provide oblique surface adversely to the inclined direction of tip of first lens tube 16A from the inner periphery of sheath tube 5A to the axis of tube 5A. In view of the refraction index of each fibre comprising light guide 20, the cross section of each fibre cut obliquely is set so that the light proceeding axially to probe 2A is refracted to viewing direction C. In such a case, the illuminating light transmitted through light guide 20 repeats total reflection from the side of each fibre so that the illuminating light radiated actually from the outlet window 44 is diverged to the periphery of viewing direction C and focussed through objective lens system 26 so as to illuminate over the observable range through the eyepiece 4.

According to the first embodiment structured as mentioned hereinabove, the outlet window for transmitting the illuminating light and for radiating the same is formed into an oblique surface inclined adversely inwards to the inclined tip of lens tube 16A so that the illuminating light transmitted through the fibres is refracted at the inclined tip to be radiated within an appropriate angular range around the viewing direction C as shown by double dotted chain line in FIG. 5.

According to the first embodiment, the observable range can be illuminated only by cutting the outlet end 44 of light guide 20 obliquely.

FIG. 6 illustrates an enlarged view in part of the top window of probe of a second embodiment of rigid endoscope of oblique window type according to the present invention.

In this embodiment, the leading end of light guide 20' comprisng a fibre bundle is cut perpendicularly to the longitudinal direction at an inner position apart from the tip of sheath tube 5A and a transparent member 51 is received within sheath tube 5A so that the trailing end of transparent member is abutted with the leading end of light guide 20'.

Transparent member 51 has a refractive index equal to or higher than that of the fibres and it is formed into outlet window 15 for radiating the illuminating light so that the outlet end 52 is cut obliquely to the inclined direciton C (to the direction crossing with the axial direction at an obtuse angle (for example, by cutting the transparent member 51 so as to have a cross section equal to that of sheath tube 5A) similarly to said first embodiment.

The functioning of the second embodiment is substantially similar to that of first embodiment.

Moreover, in the second embodiment, fibre bundle 20' may be cut obliquely and can be used in lieu of the transparent member 51. In addition, although in the first embodiment, each fibre takes a form protruded to the direction perpendicular to the axial direction of probe 2 at the inclined direction C and the obliquely cutting angle is the same for each fibre so that the fibre is protruded more forwards with the increased downward distance. The fibres are not always cut in such a manner and if the fibres have the same length and cut at the same inclined angles, the fibres show the same light distribution characteristics and such a structure falls within the range of the present invention. If the end surface has unevenness to tend the accumulation of dirt, the end surface may be sealed by a cover glass or the like.

Moreover, cross section of each fibre or the front tip of transparent member 51 is inclined at the same angle with respect to the axial direction of probe 2A, but the present invention is not limited to such a structure but includes any embodiment capable to realize the light distribution characteristics capable to illuminate the observing range by changing portionwise the angle or by arcuating portionwise the obliquely cut surfaces of fibre.

Moreover, the illuminating range around the viewing direction C may be defined by cutting the fibres obliquely or by adjusting the aperture angle incident to the fibres through condensing lens at the incident side of illuminating light.

Still further, it would be obvious that the endoscope of oblique window type is not limited to that as shown in FIG. 1

It is obvious to design various embodiments different over wide range based on the present invention without aparting from the spirit and range of the present invention. Hence, the present invention should not be restricted to any embodiment except the following claims.

What is claimed is:

1. A rigid endoscope of oblique window type having an outer tubular sheath tube, a lens tube having an optical observation system therein and extending through said tubular sheath tube, said optical observation system having an observation window at the leading, tip end of said lens tube and an optical illuminating system extending through said tubular sheath tube, said optical illuminating system terminating in an illuminating light end at the leading, tip end of said outer tubular sheath tube and adjacent said leading, tip end of said lens tube and said observation window therein, said observation window of said optical observation system being inclined in a first direction from the outer periphery of said lens tube toward the axis of said outer tubular sheath tube, said illuminating light end of said optical illuminating system being inclined in a second direction from the outer periphery of said outer tubular sheath tube and toward said observation window.

2. A rigid endoscope of oblique window type according to claim 1 characterized by that said optical observation system comprises said observation window and relay lens of refractive index ingredient type.

3. A rigid endoscope oblique window type according to claim 1 characterized by that said optical observation system comprises said observation window and a fibre bundle.

4. A rigid endoscope of oblique window type according to claim 1, 2 or 3 characterized by that said optical illuminating system comprises a fibre bundle and said fibre bundle has an oblique tip face.

5. A rigid endoscope of oblique window type according to claim 1, 2 or 3 characterized by that said optical illuminating system comprises a fibre bundle and a transparent member arranged at the front face of said fibre bundle and having an oblique tip face.

* * * * *